(12) United States Patent
Josef et al.

(10) Patent No.: US 7,060,683 B2
(45) Date of Patent: Jun. 13, 2006

(54) HYDROXAMATE-CONTAINING CYSTEINE AND SERINE PROTEASE INHIBITORS

(75) Inventors: Kurt Allen Josef, Wilmington, DE (US); John P. Mallamo, Glen Moore, PA (US); Ron Bihovsky, Wynnewood, PA (US)

(73) Assignee: Cephalon, Inc., Frazer, PA (US)

( * ) Notice: Subject to any disclaimer, the term of this patent is extended or adjusted under 35 U.S.C. 154(b) by 23 days.

(21) Appl. No.: 10/717,773

(22) Filed: Nov. 20, 2003

(65) Prior Publication Data

US 2004/0106558 A1 Jun. 3, 2004

Related U.S. Application Data

(62) Division of application No. 09/398,562, filed on Sep. 17, 1999, now Pat. No. 6,686,335.

(60) Provisional application No. 60/101,414, filed on Sep. 22, 1998.

(51) Int. Cl.
*C07K 5/06* (2006.01)

(52) U.S. Cl. .................... 514/19; 514/18; 530/331; 562/553

(58) Field of Classification Search .............. 514/19, 514/18; 530/331; 562/553
See application file for complete search history.

(56) References Cited

U.S. PATENT DOCUMENTS

| | | | |
|---|---|---|---|
| 5,514,694 A | 5/1996 | Powers et al. | 514/357 |
| 5,563,127 A | 10/1996 | Amparo et al. | 514/64 |
| 5,610,297 A | 3/1997 | Powers | 544/168 |
| 5,650,508 A | 7/1997 | Powers | 544/168 |
| 5,763,576 A | 6/1998 | Powers | 530/330 |
| 6,288,231 B1 | 9/2001 | Chatterjee et al. | 544/316 |

FOREIGN PATENT DOCUMENTS

| | | |
|---|---|---|
| WO | WO 96/39385 | 12/1996 |
| WO | WO 98/25883 | 6/1998 |

OTHER PUBLICATIONS

Chen, M., *Frontiers in Bioscience*, 1998, 3, A66-A75.
Cuzzocrea, S., et al., "Calpain inhibitor I reduces the development of acute and chronic inflammation," *Am. J. Pathol.*, Dec. 2000, 157(6), 2065-2079.
Haas, M., et al., "Effect of proteasome inhibitors on monocytic IκB-α and—β depletion, NF-κB activation, and cytokine production," *J. of Leukoc. Biol.*, Mar. 1998, 63, 395-404.
Harbeson, S.L. et al., "Stereospecific Synthesis of Peptidyl α-Keto Amides as Inhibitors of Calpain", *J. Med. Chem.*, 1994, 37, 2918-2929.
Harriman, *J. of Pharm. & Experi. Therapeu.*, 2000, 294(3), 1083-1087.
Hill, P.A., *J. Cell. Biochem.*, 1994, 56(1), 118-130.
Kavita, *J. Biol. Chem.*, 1995, 270, 27758-27765.
Kim, H., *J. of immunology*, 1995, 154(9), 4741-4748.
Kitazawa, R., et al., "Interleukin-1 receptor antagonist and tumor necrosis factor binding protein decrease osteoclast formation and bone resorption in ovariectomized mice," *J. Clin. Invest.*, Dec. 1994, 94, 2397-2406.
Mavunkel et al., "Synthesis and opioid activities of some naltrexone oxime ethers," *Eur. J. Med. Chem.*, 1994, 29, 659-666.
Meager, *Cytokine and Growth Factor Reviews*, 1999, 10, 27.
Meyer, S.L. et al., "Biologically active monomeric and heterodimeric recombinant human calpain I produced using the baculovirus expression system", *Biochem. J.*, 1996, 314, 511-519.
Miller, D.N., *FASEB J.*, 2001, 15(10), 1822-1824.
Nonaka, I., *Acta Neuropath.*, 1982, 58(4), 279-285.
Nonaka, I., *Acta Neuropath.*, 1983, 60(3-4), 167-174.
Oldgren, J., et al., *Europ. Heart J.*, 1999, 20, 1657-1666.
Read, S.J., et al., "Limiting neurological damage after stroke," *Drug & Aging*, 1999, 11-39.
Rossi, *J. of Biol. Chem.*, 1998, 273, 16446.
Rutsch, W., et al., *European Heart J.*, 1998, 19 (*Suppl. K*), K11-K17.
Saez-Torres, *Clinical and Experimental Immunology*, 2000, 121, 151.
Schaecher, K., et al., "Calpain expression and infiltration of activated T cells in experimental allergic encephalomyelitis over time: increased calpain activity begins with onset of disease," *J. of. Neuroimmunology*, 2002, 129, 1-9.
Schaecher, K.E., "The effects of calpain inhibition upon IL-2 and CD25 expression in human peripheral blood mononuclear cells," *J. of Neuroimmunology*, 2001, 119, 333-342.
Shields, D.C., et al., "Increased calpain expression in activated glial and inflammatory cells in experimental allergic encephalomyelitis," *Proc. Natl. Acad. Sci. USA*, May 1998, 95, 5768-5772.
Steinberg, *The Scientist*, 2002, 16, 22.
Steinmetzer, T., et al., *Expert Opinion on Investigational Drugs*, 2001, 10, 845-864.
Walsh, C.M., et al., "Mechanistic analysis of S-(1,2-dichlorovinyl)-L-cysteine-induced cataractogenesis *in vitro,*" *Toxcology and Appl. Pharmac.*, 1997, 146, 144-155.
Zuany-Amorim C., *European Journal of Pharmacology*, 1994, 257(3), 211-216.

*Primary Examiner*—David Lukton
(74) *Attorney, Agent, or Firm*—Woodcock Washburn LLP

(57) ABSTRACT

The present invention is directed to hydroxamate-containing inhibitors of cysteine and serine proteases. Methods for the use of the protease inhibitors are also described.

20 Claims, No Drawings

HYDROXAMATE-CONTAINING CYSTEINE AND SERINE PROTEASE INHIBITORS

CROSS REFERENCE TO RELATED APPLICATIONS

This application is a divisional of U.S. patent application Ser. No. 09/398,562, filed Sep. 17, 1999, now U.S. Pat. No. 6,686,335 which claims the benefit of U.S. Provisional Application Ser. No. 60/101,414, filed Sep. 22, 1998, each of which is incorporated by reference herein in its entirety.

FIELD OF THE INVENTION

The present invention is directed to novel inhibitors of cysteine or serine proteases, referred to herein as hydroxamates. The present invention is also directed to methods for making these novel compounds, and methods for using the same.

BACKGROUND OF THE INVENTION

Numerous cysteine and serine proteases have been identified in human tissues. A "protease" is an enzyme which degrades proteins into smaller components (peptides). The terms "cysteine protease" and "serine protease" refer to proteases which are distinguished by the presence therein of a cysteine or serine residue which plays a critical role in the catalytic process. Mammalian systems, including humans, normally degrade and process proteins via a variety of enzymes including cysteine and serine proteases. However, when present at elevated levels or when abnormally activated, cysteine and serine proteases may be involved in pathophysiological processes.

For example, calcium-activated neutral proteases ("calpains") comprise a family of intracellular cysteine proteases which are ubiquitously expressed in mammalian tissues. Two major calpains have been identified; calpain I and calpain II. While calpain II is the predominant form in many tissues, calpain I is thought to be the predominant form in pathological conditions of nerve tissues. The calpain family of cysteine proteases has been implicated in many diseases and disorders, including neurodegeneration, stroke, Alzheimer's, amyotrophy, motor neuron damage, acute central nervous system injury, muscular dystrophy, bone resorption, platelet aggregation, cataracts and inflammation. Calpain I has been implicated in excitatory amino-acid induced neurotoxicity disorders including ischemia, hypoglycemia, Huntington's Disease, and epilepsy. The lysosomal cysteine protease cathepsin B has been implicated in the following disorders: arthritis, inflammation, myocardial infarction, tumor metastasis, and muscular dystrophy. Other lysosomal cysteine proteases include cathepsins C, H, L and S. Interleukin-1β converting enzyme ("ICE") is a cysteine protease which catalyzes the formation of interleukin-1β. Interleukin-1β is an immunoregulatory protein implicated in the following disorders: inflammation, diabetes, septic shock, rheumatoid arthritis, and Alzheimer's disease. ICE has also been linked to apoptotic cell death of neurons, which is implicated in a variety of neurodegenerative disorders including Parkinson's disease, ischemia, and amyotrophic lateral sclerosis (ALS).

Cysteine proteases are also produced by various pathogens. The cysteine protease clostripain is produced by *Clostridium histolyticum*. Other proteases are produced by *Trpanosoma cruzi*, malaria parasites *Plasmodium falciparum* and *P. viznckei* and *Streptococcus*. Hepatitis A viral protease HAV C3 is a cysteine protease essential for processing of picornavirus structural proteins and enzymes.

Exemplary serine proteases implicated in degenerative disorders include thrombin, human leukocyte elastase, pancreatic elastase, chymase and cathepsin G. Specifically, thrombin is produced in the blood coagulation cascade, cleaves fibrinogen to form fibrin and activates Factor VIII; thrombin is implicated in thrombophlebitis, thrombosis and asthma. Human leukocyte elastase is implicated in tissue degenerative disorders such as rheumatoid arthritis, osteoarthritis, atherosclerosis, bronchitis, cystic fibrosis, and emphysema. Pancreatic elastase is implicated in pancreatitis. Chymase, an enzyme important in angiotensin synthesis, is implicated in hypertension, myocardial infarction, and coronary heart disease. Cathepsin G is implicated in abnormal connective tissue degradation, particularly in the lung.

Hydroxamates which are structurally distinct from the compounds disclosed herein have been described as inhibitors of glycogen phosphorylase (International Patent Application Pub. No. WO 96/39385) and thrombin (U.S. Pat. No. 5,563,127).

Given the link between cysteine and serine proteases and various debilitating disorders, compounds which inhibit these proteases would be useful and would provide an advance in both research and clinical medicine. The present invention is directed to these, as well as other, important ends.

SUMMARY OF THE INVENTION

The present invention is directed to novel cysteine and serine protease inhibitors referred to herein as hydroxamates. In preferred embodiments, the novel compounds are represented by the following Formula I:

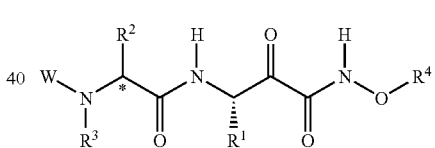

wherein:

W is A-B-D;

A is aryl$(CH_2)_n$, heteroaryl$(CH_2)_n$, alkyl having from one to about 14 carbons, alkenyl having from two to about 14 carbons, cycloalkyl having from 3 to about 10 carbons, said A group being optionally substituted with one or more J groups;

B is a bond or CO, SO, $SO_2$, OCO, $NR^5CO$, $NR^5SO_2$, or $NR^5SO$;

D is a bond, an amino acid residue, or a peptide composed of 2 to about 5 amino acid residues, said amino acid residue(s) being independently defined by the formula —NH-CH($R^6$)—CO—, in which  denotes the α carbon of an α-amino acid residue possessing, when $R^6$ is other than hydrogen, the D-configuration, the L-configuration, or a mixture of D- and L-;

n is an integer from 0 to about 6;

$R^1$, $R^2$, $R^3$, $R^4$, $R^5$ and $R^6$ are, independently, hydrogen, alkyl having from one to about 14 carbons, cycloalkyl having from 3 to about 10 carbons, said alkyl, and cycloalkyl groups being optionally substituted with one or more J groups; and J is halogen, lower alkyl, aryl, heteroaryl, haloaryl, amino optionally substituted with one to three aryl or lower alkyl groups, guanidino, alkoxycarbonyl, amido, lower alkylamido, sulfonamido, lower alkyl sulfonamido, lower alkylsulfonyl, lower alkylsulfoxy, lower alkylthio, lower alkoxy, aryloxy, arylalkyloxy, hydroxy, carboxy, cyano, or nitro; and

* denotes the α carbon of an α-amino acid residue possessing, when $R^2$ is other than hydrogen, the D-configuration, the L-configuration, or a mixture of the D- and L-configurations.

In some preferred embodiments, $R^1$ is alkyl or alkyl substituted with J, wherein J is lower alkoxy. In more preferred embodiments, $R^1$ is benzyl, methoxymethyl, or butyl.

In further preferred embodiments, $R^2$ is alkyl or alkyl substituted with J wherein J is arylallyloxy or aryl. In more preferred embodiments, $R^2$ is isobutyl or benzyloxymethyl.

In further preferred embodiments, $R^3$ is H.

In some preferred embodiments, $R^4$ is alkyl, alkyl substituted with J, cycloalkyl, or cycloalkyl substituted with J wherein J is aryl, haloaryl, alkyl or heteroaryl. More preferably, $R^4$ is methyl, ethyl, propyl, butyl, benzyl, (pentafluorophenyl)methyl, tert-butyl, or 4-methylcyclohexyl.

In some preferred embodiments, W is benzyloxycarbonyl, methanesulfonyl, benzoyl, tert-butoxycarbonyl, or benzyloxycarbonyl-leucyl.

In some preferred embodiments, $R^3$ is H, and $R^1$ is alkyl or alkyl substituted with J, wherein J is lower alkoxy.

In further preferred embodiments, $R^3$ is H, and $R^2$ is alkyl or alkyl substituted with J wherein J is arylalkyloxy or aryl.

In still further preferred embodiments, $R^3$ is H, and $R^4$ is alkyl, alkyl substituted with J, cycloalkyl, or cycloalkyl substituted with J wherein J is aryl, alkyl, haloaryl, or heteroaryl.

In still further preferred embodiments, $R^3$ is H, $R^1$ is alkyl or alkyl substituted with J, wherein J is lower alkoxy, and $R^2$ is alkyl or alkyl substituted with J wherein J is arylalkyloxy or aryl.

In still further preferred embodiments, $R^3$ is H, $R^1$ is alkyl or alkyl substituted with J, wherein J is lower alkoxy, and $R^4$ is alkyl, alkyl substituted with J, cycloalkyl, or cycloalkyl substituted with J wherein J is aryl, haloaryl, alkyl or heteroaryl.

In further preferred embodiments, $R^3$ is H, $R^1$ is alkyl or alkyl substituted with J, wherein J is lower alkoxy, $R^4$ is alkyl, alkyl substituted with J, cycloalkyl, or cycloalkyl substituted with J wherein J is aryl, haloaryl, alkyl or heteroaryl, and $R^2$ is alkyl or alkyl substituted with J wherein J is arylalkyloxy or aryl.

In some particularly preferred embodiments, $R^1$ is benzyl, methoxymethyl, or butyl; $R^2$ is isobutyl or benzyloxymethyl; $R^3$ is hydrogen; $R^4$ is methyl, ethyl, propyl, butyl, benzyl, (pentafluorophenyl)methyl, tert-butyl, or 4-methylcyclohexyl; and W is benzyloxycarbonyl, methanesulfonyl, benzoyl, tert-butoxycarbonyl, or benzyloxycarbonyl-leucyl.

In further particularly preferred embodiments, $R^1$ is benzyl; $R^2$ is isobutyl; * denotes the α carbon of an α-amino acid residue possessing the L-configuration; $R^3$ is hydrogen; $R^4$ is methyl, ethyl, propyl, butyl, benzyl, (pentafluorophenyl)methyl, tert-butyl, or 4-methylcyclohexyl; and W is benzyloxycarbonyl or benzyloxycarbonyl-leucyl.

In further particularly preferred embodiments, $R^1$ is benzyl; $R^2$ is benzyloxymethyl; * denotes the α carbon of an α-amino acid residue possessing the D-configuration; $R^3$ is hydrogen; $R^4$ is methyl, ethyl, or benzyl; and W is methanesulfonyl.

Some especially preferred embodiments of the invention are described in Table 1, infra.

The present invention also provides compositions for inhibiting a protease selected from the group consisting of serine proteases and cysteine proteases comprising a compound of the invention.

Also provided by the present invention are methods for inhibiting a protease comprising contacting a protease selected from the group consisting of serine proteases and cysteine proteases with an inhibitory amount of a compound of the invention, and methods for inhibiting a protease comprising contacting a protease selected from the group consisting of serine proteases and cysteine proteases with an inhibitory amount of a composition comprising a compound of the invention.

The compounds of the invention are useful for inhibition of cysteine and serine proteases. Beneficially, these compounds find utility in a variety of settings. For example, in the research arena, the claimed compounds can be used, for example, in discovery of agents for treating disorders associated with abnormal and/or aberrant activity of cysteine and/or serine proteases. In a clinical arena, for example, the compounds can be used to alleviate, mediate, reduce, and/or prevent disorders which are associated with abnormal and/or aberrant activity of cysteine and/or serine proteases.

Thus, in some preferred embodiments, the present invention further provides pharmaceutical compositions comprising a compound of the invention, preferably also containing a pharmaceutically acceptable carrier. Also provided in accordance with the present invention are compositions for the treatment of a disorder, which is preferably neurodegeneration, stroke, Alzheimer's, amyotrophy, motor neuron damage, acute central nervous system injury, muscular dystrophy, bone resorption, platelet aggregation, cataracts and inflammation, comprising a compound of claim 1 and a pharmaceutically effective carrier. The present invention also provides methods for the treatment of a disorder, which is preferably neurodegeneration, stroke, Alzheimer's, amyotrophy, motor neuron damage, acute central nervous system injury, muscular dystrophy, bone resorption, platelet aggregation, cataracts and inflammation, comprising administering to a subject in need of such treatment an effective amount of a compound of the invention Because the hydroxamates of the invention inhibit cysteine proteases and serine proteases, they can be used in both research and therapeutic settings. These and other features of the compounds of the subject invention are set forth in more detail below.

DETAILED DESCRIPTION

The present invention provides novel inhibitors of cysteine and serine protease inhibitors. In preferred embodiments, the compounds of the invention have the Formula I:

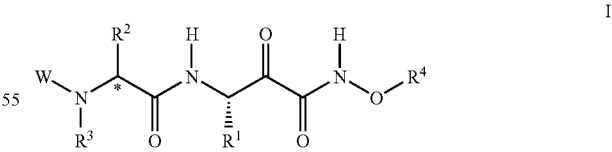

wherein:

W is A-B-D;

A is aryl$(CH_2)_n$, heteroaryl$(CH_2)_n$, alkyl having from one to about 14 carbons, alkenyl having from two to about 14 carbons, cycloalkyl having from 3 to about 10 carbons, said A group being optionally substituted with one or more J groups;

B is a bond or CO, SO, $SO_2$, OCO, $NR^5CO$, $NR^5SO_2$, or $NR^5SO$;

D is a bond, an amino acid residue, or a peptide composed of 2 to about 5 amino acid residues, said amino acid residue(s) being independently defined by the formula —NH-CH($R^6$)—CO—, in which  denotes the α carbon of an α-amino acid residue possessing, when $R^6$ is other than hydrogen, the D-configuration, the L-configuration, or a mixture of D- and L-;

n is an integer from 0 to about 6;

$R^1$, $R^2$, $R^3$, $R^4$, $R^5$ and $R^6$ are, independently, hydrogen, alkyl having from one to about 14 carbons, cycloalkyl having from 3 to about 10 carbons, said alkyl, and cycloalkyl groups being optionally substituted with one or more J groups; and J is halogen, lower alkyl, aryl, heteroaryl, haloaryl, amino optionally substituted with one to three aryl or lower alkyl groups, guanidino, alkoxycarbonyl, arido, lower alkylamido, sulfonamido, lower alkyl sulfonamido, lower alkylsulfonyl, lower alkylsulfoxy, lower alkylthio, lower alkoxy, aryloxy, arylalkyloxy, hydroxy, carboxy, cyano, or nitro; and

* denotes the α carbon of an α-amino acid residue possessing, when $R^2$ is other than hydrogen, the D-configuration, the L-configuration, or a mixture of the D- and L-configurations.

The compounds of the invention are useful in a variety of settings. For example, in a research environment, preferred compounds having defined attributes can be used to screen for natural and synthetic compounds which evidence similar characteristics in inhibiting protease activity. Inhibition of cysteine protease or serine protease activity can be measured by determining the rate of inactivation of a protease using a compound of the invention. The compounds can also be used in the refinement of in vitro and in vivo models for determining the effects of inhibition of particular proteases on particular cell types or biological conditions. In a therapeutic setting, given the connection between cysteine proteases and certain defined disorders, and serine proteases and certain defined disorders, compounds of the invention can be utilized to alleviate, mediate, reduce and/or prevent disorders which are associated with abnormal and/or aberrant activity of cysteine proteases and/or serine proteases.

As used herein, the term "alkyl" is meant to include straight-chain, branched and cyclic hydrocarbon groups such as, for example, ethyl, and isopropyl groups. Preferred alkyl groups have 1 to about 10 carbon atoms. The term "lower alkyl" refers to alkyl groups of 1–6 carbon atoms. In general, the term "lower" refers to groups having up to six carbon atoms. The term "cycloalkyl" denotes cyclic aillyl gorups, such as, for example, cyclopropyl groups. The term "alkenyl" denotes alkyl groups that contain at least one double bond. "Aryl" groups are aromatic cyclic compounds including but not limited to phenyl, tolyl, naphthyl, anthracyl, phenanthryl, pyrenyl, and xylyl. Preferred aryl groups include phenyl and naphthyl.

In general, the term "hetero" when used as a prefix denotes the presence of one or more hetero atoms such as O, N or S. Thus, the term "heterocyclic" refers to cyclic groups in which the ring portion includes at least one heteroatom. "Heteroalkyl" groups are heterocycles containing solely single bonds within their ring portions, i.e. saturated heteroatomic ring systems. The term "heteroaryl" denotes aryl groups wherein at least one ring carbon has been replaced with a hetero atom. The term "haloaryl" is intended to mean an aryl group that bears one or more halogen atoms. The term "halogen" refers to F, Cl, Br, and I atoms.

As used herein, "alkoxy" groups are alkyl groups linked through an oxygen atom. Examples of alkoxy groups include methoxy (—$OCH_3$) and ethoxy (—$OCH_2CH_3$) groups. In general, the term "oxy" when used as a suffix denotes attachment through an oxygen atom. Thus, alkoxycarbonyl groups are carbonyl groups which contain an alkoxy substituent, i.e., groups of general formula —C(=O)—O—R, where R is alkyl. The term "aryloxy" denotes an aryl group linked through an oxygen atom. The term "arylalkyl" (or "aralkyl") denotes an alkyl group that bears an aryl substituent. The term "arylalkyloxy (or "aralkyloxy") denotes an aralkyl group linked through an oxygen atom.

As used herein, the term "amino acid" denotes a molecule or residue thereof containing both an amino group and a carboxyl group. As used herein the term "α-amino acid" means an amino acid of general formula HOOC—CH (sidechain)-$NH_2$, or a residue of such amino acid of formula, for example, —C(=O)—CH(sidechain)-NH—. In preferred embodiments of the compounds of the invention, the α-carbon (i.e., the carbon that bears the sidechain) of constituent amino acids can be exclusively in the L-configuration, exclusively in the D-configuration, or in a mixture of D and L configurations in any proportion.

Functional groups present on the compounds of Formula I may contain protecting groups. For example, the amino acid sidechain substituents of the compounds of Formula I can be substituted with protecting groups such as benzyloxycarbonyl or t-butoxycarbonyl groups. Protecting groups are known per se as chemical finctional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. One such protecting group is the benzyloxycarbonyl (Cbz; Z) group. Other preferred protecting groups according to the invention may be found in Greene, T. W. and Wuts, P. G. M., "*Protective Groups in Organic Synthesis*" 2d. Ed., Wiley & Sons, 1991.

As used herein, the term "amido" has its accustomed meaning as a group of formula —C(=O)—NH—. The term "alkylamido" denotes an amido grouop that bears an alkyl substituent. The term "sulfonamido" denotes a group of formula —$SO_2$—NH—. In general, the terrm "alkyl" or "aryl" when used as a prefix in such terms as "alkylsulfonamido," "alkylsulfonyl," "alkylsulfoxy" or "alkylthio" indicates that the sulfonamido, sulfonyl, sulfoxy or thio group bears an alkyl substituent.

Some constituent groups represented in the Formulas described herein can be substituted. As used herein, the term "substituted" indicates that any available hydrogen atom of the moiety designated as "substituted" can be replaced by the indicated group.

In preferred embodiments, compositions are provided for inhibiting a serine protease or a cysteine protease comprising a compound of the invention. In other preferred embodiments, methods are provided for inhibiting serine proteases or cysteine proteases comprising contacting a protease selected from the group consisting of serine proteases and cysteine proteases with an inhibitory amount of a compound of the invention.

The disclosed compounds of the invention are useful for the inhibition of cysteine proteases and serine proteases. As used herein, the terms "inhibit" and "inhibition" mean having an adverse effect on enzymatic activity. An inhibitory amount is an amount of a compound of the invention effective to inhibit a cysteine and/or serine protease.

Pharmaceutically acceptable salts of the cysteine and serine protease inhibitors also fall within the scope of the compounds as disclosed herein. The term "pharmaceutically acceptable salts" as used herein means an inorganic acid addition salt such as hydrochloride, sulfate, and phosphate, or an organic acid addition salt such as acetate, maleate, fumarate, tartrate, and citrate. Examples of pharmaceutically acceptable metal salts are alkali metal salts such as sodium salt and potassium salt, alkaline earth metal salts such as magnesium salt and calcium salt, aluminum salt, and zinc salt. Examples of pharmaceutically acceptable ammonium salts are ammonium salt and tetramethylammonium salt. Examples of pharmaceutically acceptable organic amine addition salts are salts with morpholine and piperidine. Examples of pharmaceutically acceptable amino acid addition salts are salts with lysine, glycine, and phenylalanine.

Compounds provided herein can be formulated into pharmaceutical compositions by admixture with pharmaceutically acceptable nontoxic excipients and carriers. As noted above, such compositions may be prepared for use in parenteral administration, particularly in the form of liquid solutions or suspensions; or oral administration, particularly in the form of tablets or capsules; or intranasally, particularly in the form of powders, nasal drops, or aerosols; or dermally, via, for example, transdermal patches; or prepared in other suitable fashions for these and other forms of administration as will be apparent to those skilled in the art.

The composition may conveniently be administered in unit dosage form and may be prepared by any of the methods well known in the pharmaceutical art, for example, as described in *Remington's Pharmaceutical Sciences* (Mack Pub. Co., Easton, Pa., 1980). Formulations for parenteral administration may contain as common excipients sterile water or saline, polyalkylene glycols such as polyethylene glycol, oils and vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the active compounds. Other potentially useful parenteral delivery systems for these active compounds include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, a salicylate for rectal administration, or citric acid for vaginal administration. Formulations for transdermal patches are preferably lipophilic emulsions.

The materials of this invention can be employed as the sole active agent in a pharmaceutical or can be used in combination with other active ingredients, e.g., other growth factors which could facilitate neuronal survival or axonal regeneration in diseases or disorders.

The concentrations of the compounds described herein in a therapeutic composition will vary depending upon a number of factors, including the dosage of the drug to be administered, the chemical characteristics (e.g., hydrophobicity) of the compounds employed, and the route of administration. In general terms, the compounds of this invention may be provided in effective inhibitory amounts in an aqueous physiological buffer solution containing about 0.1 to 10% w/v compound for parenteral administration. Typical dose ranges are from about 1 mg/kg to about 1 g/kg of body weight per day; a preferred dose range is from about 0.01 mg/kg to 100 mg/kg of body weight per day. Such formulations typically provide inhibitory amounts of the compound of the invention. The preferred dosage of drug to be administered is likely, however, to depend on such variables as the type and extent of progression of the disease or disorder, the overall health status of the particular patient, the relative biological efficacy of the compound selected, and formulation of the compound excipient, and its route of administration.

As used herein, the term "contacting" means directly or indirectly causing at least two moieties to come into physical association with each other. Contacting thus includes physical acts such as placing the moieties together in a container, or administering moieties to a patient. Thus, for example administering a compound of the invention to a human patient evidencing a disease or disorder associated with abnormal and/or aberrant activity of such proteases falls within the scope of the definition of the term "contacting".

The invention is further illustrated by way of the following examples which are intended to elucidate the invention. These examples are not intended, nor are they to be construed, as limiting the scope of the disclosure.

EXAMPLES

General Methods

Thin layer chromatography was performed using silica gel coated plates (MK6F 60A, size 1×3 in, layer thickness 250 μm, Whatman Inc.). Preparative thin layer chromatography was performed using silica gel coated plates (size 20×20 cm, layer thickness 1000 micron, Analtech). Preparative column chromatography was carried out using Merck silica gel, 40–63 μm, 230–400 mesh. $^1$H NMR spectra were recorded on a GE QE300 Plus spectrometer at 300 MHz using tetramethylsilane as internal standard. Electrospray mass spectra were recorded on a VG platform II instrument (Fisons Instruments).

Examples 1–15 were prepared following General Method A or B.

General Method A

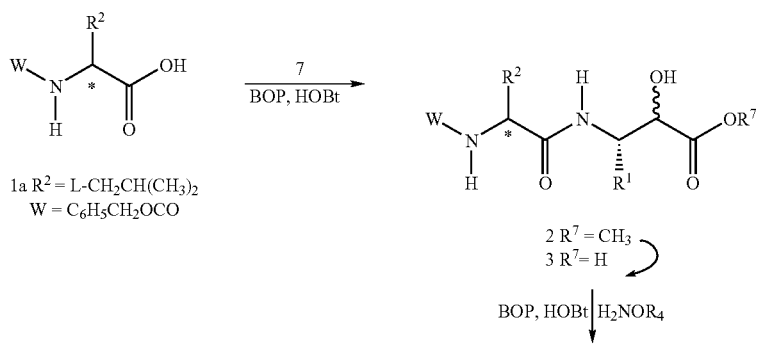

-continued
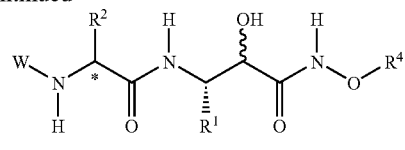
4a R⁴ = CH₃
Dess-Martin ↓
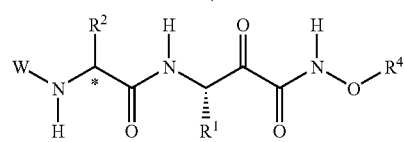
5a R¹ = CH₂C₆H₅; R² = L - CH₂CH(CH₃)₂
W = C₆H₅CH₂OCO; R⁴ = CH₃
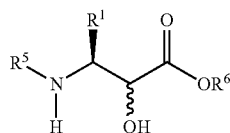
6a R¹ = CH₂C₆H₅; R₅ = tBOC; R⁶ = H
7 R¹ = CH₂C₆H₅; R⁵ = H•HCl; R⁶ = CH₃
General Method B
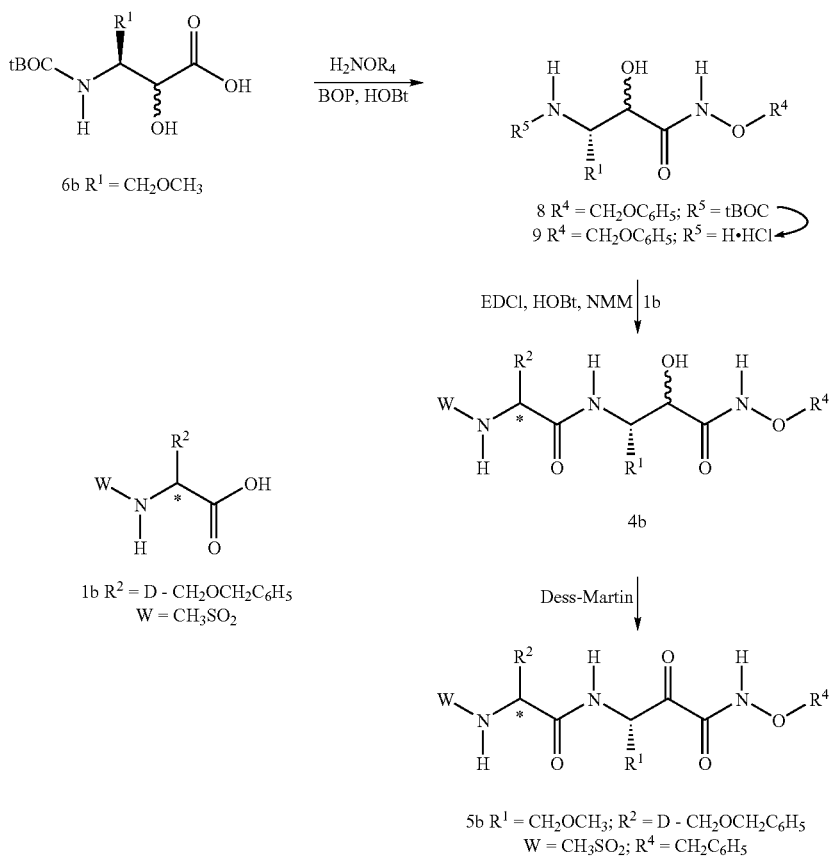

Compounds 6a, 6b and related hydroxyacids, were synthesized following a general procedure of Harbeson et al., *J. Med. Chem.* 1994, 37, 2918–2929.

Example 1

Cbz-Leu-Phe-CONHOCH₃ (General Method A)

Compound 5a

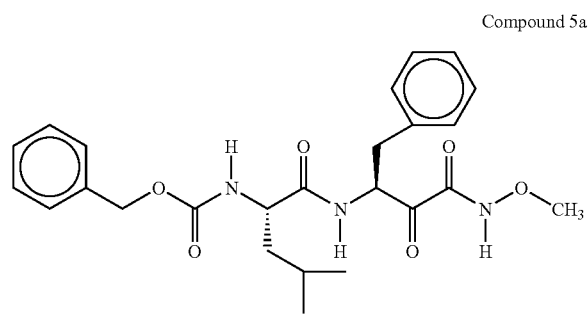

To a cooled (0° C.) solution of compound 6a (500 mg, 1.69 mmole) in anhydrous methanol (25 ml) was added slowly thionyl chloride (0.37 ml, 5.08 mmole). The mixture was then stirred at ambient temperature for 16 hours and concentrated under reduced pressure. Trituration with ethyl ether gave compound 7 that was dried and used directly in the next step. White solid; $^1$H NMR (DMSO-d$_6$) d 8.49 (br, 1H), 8.15 (br, 2H), 7.22 (m, 10H), 6.52 (dd, 1H), 4.35 (ddd, 1H), 3.80 (ddd, 1H), 3.28 (d, 3H), 3.08 (dd, 1H), 2.80 (dd, 1H). MS m/e 210 (M+H).

To a solution of compound 1a (450 mg, 1.69 mmole) in anhydrous DMF (5 ml), was added 1-HOBt (229 mg, 1.69 mmole), BOP (899 mg, 2.03 mmole), and N-methylmorpholine (0.74 ml, 6.78 mmole). After 5 min., compound 7 (416 mg, 1.69 mmole) dissolved in 5 ml DMF was added. Stirring was continued 90 min at ambient temperature. The mixture was poured into water (50 ml) and was extracted into ethyl acetate (3×20 ml). The organic layer was washed with 3% citric acid solution (10 ml), saturated sodium bicarbonate solution (10 ml), and brine (10 ml). The solution was dried over MgSO$_4$, filtered and concentrated under reduced pressure to afford 700 mg crude product. Preparative column chromatography (1–5% MeOH/methylene chloride) afforded 533 mg of compound 2 (69%). White amorphous solid; $^1$H NMR (DMSO-d$_6$) δ 8.2 (d, 2H), 8.0 (m, 2H), 7.0 (s, 3H). MS m/e 457 (M+H).

To a cooled (0° C.) solution of compound 2 (533 mg, 1.17 mmole) in methanol (10 ml) was added slowly 1N NaOH solution (2.92 ml, 2.92 mmole). The mixture was then stirred at ambient temperature for 90 minutes and concentrated under reduced pressure. Water (30 ml) was added and the mixture was extracted with diethyl ether (30 ml). The aqueous portion was acidified to pH=4 with solid citric acid and extracted with ethyl acetate (3×20 ml). The solution was dried over MgSO$_4$, filtered and concentrated under reduced pressure to afford 439 mg compound 3 (85%). No futher purification was nesseccary. White amorphous solid; $^1$H NMR (DMSO-d$_6$) δ 7.73 (dd, 1H); 7.31 (m, 10H), 5.07 (s, 2H), 4.17 (m, 1H), 4.04 (m, 2H), 3.41 (m, 1H), 2.88 (m, 1H), 2.74 (m, 2H), 1.58 (m, 1H), 1.33 (m, 2H), 0.85 (m, 6H). MS m/e 441 (M−H).

To a solution of compound 3 (125 mg, 0.283 mmole) in anhydrous DMF (5 ml), was added 1-HOBt (38 mg, 0.283 mmole), BOP (150 mg, 0.339 mmole), and N-methylmorpholine (0.109 ml, 0.99 mmole). After 5min., H$_2$NOMe.HCl (27 mg, 0.283 mmole) dissolved in 5 ml DMF was added. Stirring was continued 90 min at ambient temperature. The mixture was poured into water (50 ml) and was extracted into ethyl acetate (3×20 ml). The organic layers were washed with 3% citric acid solution (10 ml), saturated sodium bicarbonate solution (10 ml), and brine (10 ml). The solution was dried over MgSO$_4$, filtered and concentrated under reduced pressure to afford 110 mg crude product. Chromatography with preparative thin layer plates (5% MeOH/ methylene chloride) afforded 79 mg of compound 4a (59%). White amorphous solid; MS m/e 472 (M+H).

To a cooled (0° C.) solution of compound 4a (79 mg, 0.168 mmole) in anhydrous methylene chloride (10 ml) was slowly added Dess-Martin periodinane reagent (71 mg, 0.168 mmole). The cooling bath was removed and the mixture was stirred an additional 90 minutes. The mixture was then washed with 10% sodium thiosulfate solution (2×10 ml), saturated sodium bicarbonate solution (5 ml), and brine (5 ml). The solution was dried over MgSO$_4$, filtered and concentrated under reduced pressure to afford 60 mg compound 5a (76%). White amorphous solid; $^1$H NMR (CDCl$_3$) δ 9.55 (br s, 1H), 7.20 (m, 10H), 6.82 (d, 1H), 5.40 (m, 1H), 5.03 (s, 2H), 4.95 (br s, 1H), 4.14 (m, 1H), 3.81 (s, 3H), 3.24 (dd, 1H), 2.96 (dd, 1H), 1.52 (m, 2H), 1.39 (m, 1H), 0.83 (m, 6H). MS m/e 470 (M+H).

Example 2

Cbz-Leu-Phe-CONHOEt

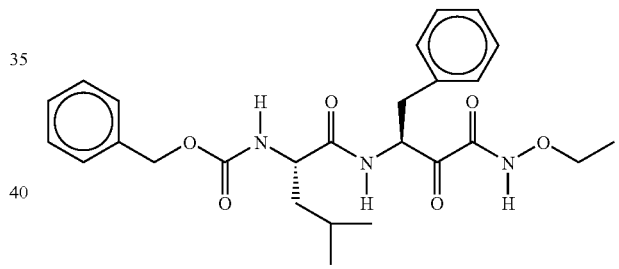

This compound was prepared by General Method A from commercially available H$_2$NOEt.HCl.

$^1$H NMR (DMSO-d$_6$) δ 8.38 (d, 1H), 7.25 (m, 10H), 5.13 (m, 1H), 5.03 (s, 2H), 4.09 (m, 1H), 3.83 (q, 2H), 3.11 (dd, 1H), 2.87 (dd, 1H), 1.59 (m, 1H), 1.38 (m, 2H), 1.18 (t, 3H), 0.86 (m, 6H). MS m/e 484 (M+H).

Example 3

Cbz-Leu-Phe-CONHOBn

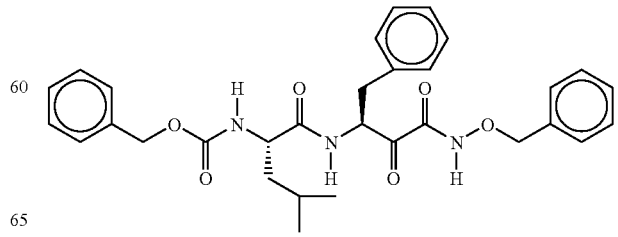

This compound was prepared by General Method A from commercially available H$_2$NOBn.HCl.

$^1$H NMR (CDCl$_3$) δ 9.39 (br s, 1H), 7.25 (m, 15H), 6.82 (d, 1H), 5.45 (m, 1H), 5.08 (s, 2H), 5.03 (br, 1H), 4.99 (dd, 2H), 4.18 (m, 1H), 3.32 (dd, 1H), 3.07 (dd, 1H), 1.86 (m, 2H), 1.44 (m, 1H), 0.85 (m, 6H). MS m/e 546 (M+H).

Example 4

Cbz-Leu-Phe-CONHOCH$_2$C$_6$F$_5$

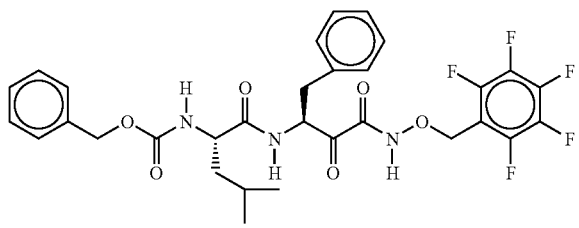

This compound was prepared by General Method A from commercially available H$_2$NOCH$_2$C$_6$F$_5$.HCl.

$^1$H NMR (CDCl$_3$) δ 9.76(br s, 1H), 7.23 (m, 10H), 6.74 (d, 1H), 5.42 (m, 1H), 5.08 (m, 4H), 5.00 (br s, 1H), 4.18 (m, 1H), 3.24 (dd, 1H), 2.95 (dd, 1H), 1.60 (m, 2H), 1.42 (m, 1H), 0.82 (m, 6H). MS m/e 636 (M+H).

Example 5

Cbz-Leu-Phe-CONHOtBu

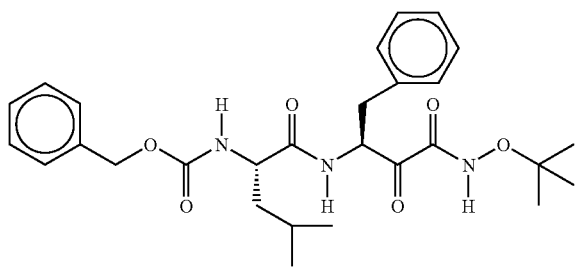

This compound was prepared by General Method A from commercially available H$_2$NOtBu.HCl.

$^1$H NMR (CDCl$_3$) δ 8.88 (br s, 1H), 7.25 (m, 10H), 6.62 (m, 1H), 5.42 (m, 1H), 5.08 (s, 2H), 4.18 (m, 1H), 3.35 (dd, 1H), 3.10 (dd, 1H), 1.60 (m, 3H), 1.38 (s, 9H), 0.85 (m, 6H). MS m/e 512 (M+H).

Additional O-substituted hydroxylamines were prepared using the procedure of Mavunkel et al, *Eur. J Med. Chem.* 1994, 29, 659–666.

Example 6

Cbz-Leu-Phe-CONHO(4-methylcyclohexane)

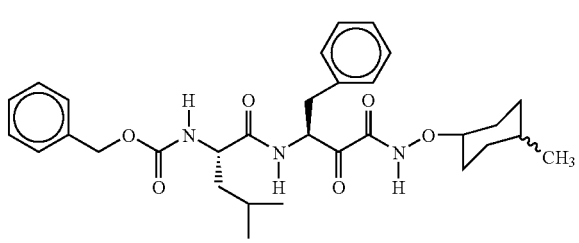

This compound was prepared by General Method A from [(4-methylcyclohexyl)oxy]amine.

$^1$H NMR (CDCl$_3$) δ 9.54 (d, 1H), 7.25 (m, 10H), 6.84 (m, 1H), 5.44 (m, 1H), 5.22 (m, 1H), 5.08 (dd, 2H), 4.18 (m, 2H), 3.30 (m, 1H), 3.00 (m, 1H), 2.04 (m, 2H), 1.42 (m, 9H), 0.80 (m, 9H). MS m/e 552 (M+H).

Example 7

CH$_3$SO$_2$-D-Ser(Bn)-Ser(Me)-CONHOBn (General Method B)

Compound 5b

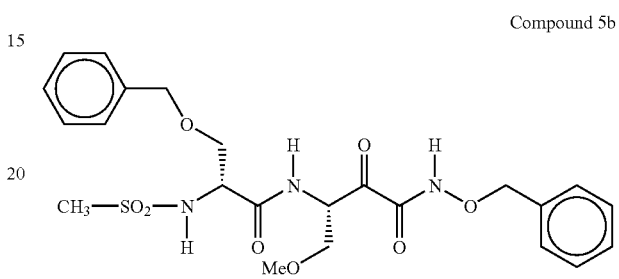

To a suspension of D-Ser(Bn) (2.0 g, 10.3 mmole) in water (10 ml) was added 1N NaOH solution (20 ml). After the solids had dissolved, methanesulfonyl chloride (1.19 ml, 15.5 mmole) was added slowly. Additional 1N NaOH (5 ml) was added to adjust the pH=10. The mixture was stirred 16 hours at ambient temperature, and then acidified to pH=2 with concentrated HCl solution. The mixture was extracted into ethyl acetate (3×50 ml) and the washed with brine (30 ml). The solution was dried over MgSO$_4$, filtered and concentrated under reduced pressure to afford 1.9 g (68%) of compound 1b as a white solid. No further purification was necessary. White amorphous solid; $^1$H NMR (CDCl$_3$) δ 7.26 (m, 5H), 5.30 (d, 1H), 4.55 (s, 2H), 4.37 (m, 1H), 3.95 (dd, 1H), 3.75 (dd, 1H), 3.00 (s, 3H). MS m/e 272 (M−H).

To a solution of compound 6b (185 mg, 0.743 mmole) in anhydrous DMF (5 ml), was added 1-HOBt (100 mg, 0.743 mmole), BOP (394 mg, 0.892 mmole), and N-methylmorpholine (0.285 ml, 2.60 mmole). After 5 min., H$_2$NOBn.HCl (119 mg, 0.743 mmole) dissolved in 5 ml DMF was added. Stirring was continued 90 min at ambient temperature. The mixture was poured into water (30 ml) and was extracted into ethyl acetate (3×20 ml). The organic layer was washed with 3% citric acid solution (5 ml), saturated sodium bicarbonate solution (5 ml), and brine (5 ml). The solution was dried over MgSO$_4$, filtered and concentrated under reduced pressure to afford 400 mg crude product. Chromatography with preparative thin layer plates (5% MeOH/methylene chloride) afforded 189 mg of compound 8 (71%). White amorphous solid; $^1$H NMR (CDCl$_3$) δ 7.26 (m, 5H), 5.30 (d, 1H), 4.55 (s, 2H), 4.37 (m, 1H), 3.95 (dd, 1H), 3.75 (dd, 1H), 3.00 (s, 3H). MS m/e 355 (M+H).

To a cooled (0° C.) solution of compound 8 (189 mg, 0.534 mmole) in anhydrous ethyl acetate (10 ml) was slowly bubbled anhydrous HCl for a period of 15 seconds. The mixture was then stirred at ambient temperature for 60 minutes and concentrated under reduced pressure. Trituration with ethyl ether gave compound 9 that was dried and used directly in the next step. White amorphous solid; MS m/e 255 (M+H).

A solution of compound 9 (82 mg, 0.282 mmole) and N-methylmorpholine (0.031 ml, 0.282 mmole) in anhydrous DMF (10 ml) was stirred 5 minutes. To this solution was added compound 1b (77 mg, 0.282 mmole), 1-HOBt (38 mg, 0.282 mmole), and EDCI (65 mg, 0.338 mmole). The mixture was stirred 16 hours at ambient temperature, poured into water (30 ml) and was extracted into ethyl acetate (5×20 ml). The organic layer was washed with 3% citric acid solution (5 ml), saturated sodium bicarbonate solution (5 ml), and brine (5 ml). The solution was dried over $MgSO_4$, filtered and concentrated under reduced pressure to afford 50 mg crude product. Chromatography with preparative thin layer plates (5% MeOH/methylene chloride) afforded 25 mg of compound 4b (17%). White amorphous solid; MS m/e 510 (M+H).

To a cooled (0° C.) solution of compound 4b (25 mg, 0.049 mmole) in anhydrous methylene chloride (10 ml) was slowly added Dess-Martin periodinane reagent (31 mg, 0.074 mmole). The cooling bath was removed and the mixture was stirred an additional 90 minutes. The mixture was then washed with 10% sodium thiosulfate solution (2×5 ml), saturated sodium bicarbonate solution (2 ml), and brine (2 ml). The solution was dried over $MgSO_4$, filtered and concentrated under reduced pressure to afford 14 mg of compound 5b (56%). White amorphous solid; $^1$H NMR (CDCl$_3$) δ 9.09 (br, 1H), 7.25 (m, 11H), 5.45 (m, 1H), 5.28 (m, 1H), 4.94 (dd, 2H), 4.55 (dd, 2H), 4.15 (m, 2H), 3.88 (m, 1H), 3.66 (m, 2H), 3.23 (s, 3H), 2.95 (s, 3H). MS m/e 508 (M+H).

Example 8

CH$_3$SO$_2$-D-Ser(Bn)-Phe-CONHOBn

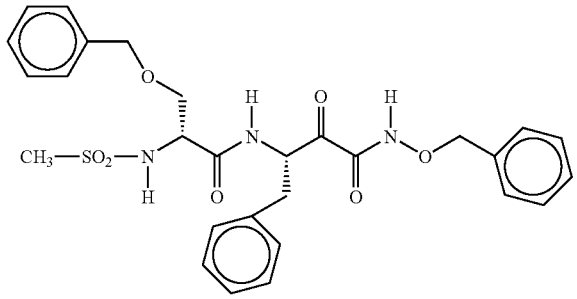

This compound was prepared by General Method A.
$^1$H N (CDCl$_3$) δ 9.53 (m, 1H), 7.25 (m, 16H), 5.49 (m, 1H), 4.92 (m, 2H), 4.40 (dd, 2H), 4.18 (m, 2H), 3.55 (m, 2H), 2.81 (s, 3H), 2.72 (m, 2H). MS m/e 554 (M+H).

Example 9

CH$_3$SO$_2$-D-Ser(Bn)-Ser(Me)-CONHOEt

This compound was prepared by General method A.
$^1$H NMR (CDCl$_3$) δ 9.38 (d, 1H), 7.21 (m, 1 1H), 5.49 (m, 1H), 5.37 (m, 1H), 4.49 (dd, 2H), 4.09 (q, 2H), 3.82 (m, 1H), 3.61 (m, 1H), 3.35 (m, 1H), 3.18 (m, 1H), 2.93 (s, 3H), 1.38 (t, 3H). MS m/e 492 (M+H).

Example 10

Cbz-Val-Phe-CONHOBn

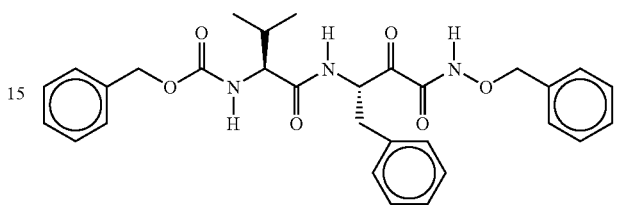

This compound was prepared by General Method B.
$^1$H NMR (CDCl$_3$) δ 9.34 (br s, 1H), 7.25 (m, 15H), 6.82 (d, 1H), 5.45 (m, 1H), 5.08 (s, 2H), 5.03 (br, 1H), 4.99 (dd, 2H), 4.18 (m, 1H), 3.32 (dd, 1H), 3.07 (dd, 1H), 1.44 (m, 1H), 0.87 (m, 6H). MS m/e 532 (M+H).

Example 11

Cbz-Val-Nle-CONHOBn

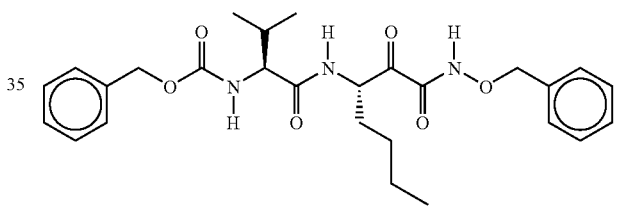

This compound was prepared by General Method B.
$^1$H NMR (CDCl$_3$) δ 9.46 (br s, 1H), 7.20 (m, 10H), 6.85 (d, 1H), 5.45 (m, 1H), 5.11 (s, 2H), 5.01 (br, 1H), 4.92 (m, 1H), 4.15 (m, 1H), 3.20 (br, 2H), 1.40 (m, 15H). MS m/e 498 (M+H).

Example 12

Cbz-Leu-Leu-Phe-CONHOCH$_3$

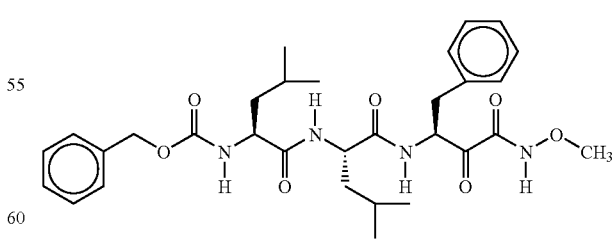

This compound was prepared by General Method A.
$^1$H NMR (CDCl$_3$) δ 9.48 (s, 1H), 7.24 (m, 10H), 6.92 (d, 1H), 6.50 (d, 1H), 5.38 (m, 1H), 5.09 (s, 2H), 4.39 (m, 1H), 4.16 (m, 2H), 3.78 (s, 3H), 3.26 (dd, 1H), 3.02 (dd, 1H), 2.02 (m, 1H), 1.42 (m, 5H), 0.83 (m, 12H). MS m/e 583 (M+H).

Example 13

Cbz-Leu-Leu-Phe-CONHOBn

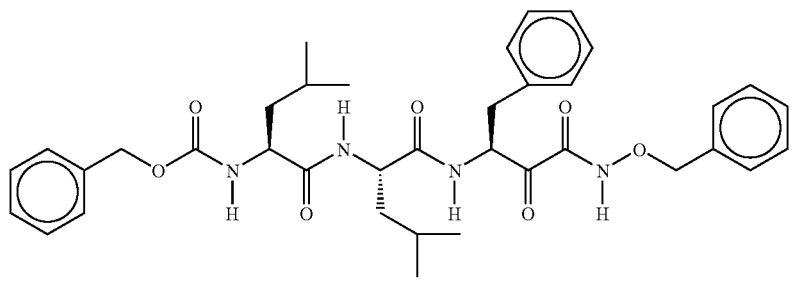

This compound was prepared by General Method A.

¹H NR (CDCl₃) δ 9.48 (s, 1H), 7.24 (m, 15H), 6.78 (d, 1H), 6.58 (d, 1H), 5.43 (m, 1H), 5.21 (m, 1H), 5.09 (s, 2H); 4.94 (dd; 2H), 4.42 (m, 1H, 4.16 (m, 1H), 3.26 (dd, 1H), 3.02 (dd, 1H), 2.02 (m, 1H), 1.42 (m, 5H), 0.83 (m, 12H). MS m/e 659 (M+H).

Example 14

Cbz-Leu-Phe-CONHOBu

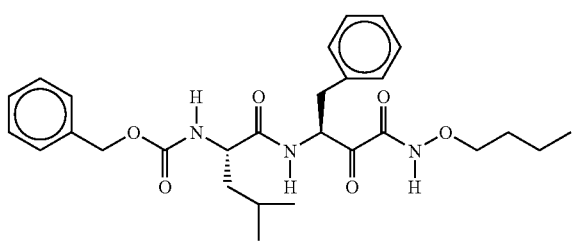

This compound was prepared by General Method A.

¹H NMR (CDCl₃) δ 9.21 (br s, 1H), 7.26 (m, 10H), 6.82 (d, 1H), 5.40 (m, 1H), 5.08 (s, 2H), 4.14 (m, 1H), 3.68 (m, 2H), 3.35. (m, 1H), 3.02 (m, 1H), 1.39 (m, 7H), 0.83 (m, 9H). MS m/e 512 (M+H).

Example 15

PhCO-Phe-Nle-CONHOEt

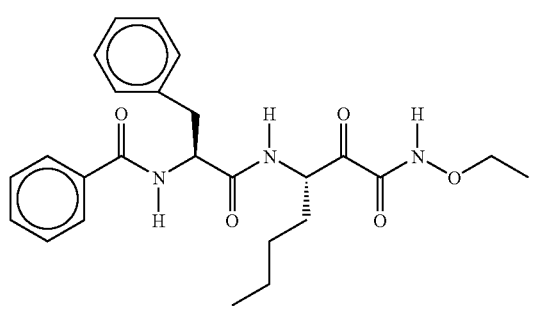

This compound was prepared by General Method B.

¹H NMR (CDCl₃) δ 9.12 (d, 1H), 7.40 (m, 10H), 6.75 (d, 1H), 5.38 (m, 1H), 5.13 (m, 1H), 4.87 (m, 1H), 4.25 (m, 1H), 4.17 (m, 1H), 4.02 (m, 2H), 3.20 (m, 2H), 2.35 (m, 2H), 1.40 (m, 8H). MS m/e 454 (M+H).

Example 16

Inhibition of Calpain

To evaluate inhibitory activity, stock solutions (40 times concentrated) of each compound to be tested were prepared in 100% anhydrous DMSO and 5 μL of each inhibitor preparation were aliquoted into each of three wells of a 96-well plate. Recombinant human calpain I, prepared by the method of Meyer et al. (*Biochem., J.* 1996, 314: 511–519), was diluted into assay buffer (i.e., 50 mM Tris, 50 mM NaCl, 1 mM EDTA, 1 mM EGTA, and 5 mM β-mercaptoethanol, pH 7.5, including 0.2 mM Succ-Leu-Tyr-MNA), and 175 μl was aliquoted into the same wells containing the independent inhibitor stocks as well as to positive control wells containing 5 μl DMSO, but no compound. To start the reaction, 20 μl of 50 mM CaCl₂ in assay buffer was added to all wells of the plate, excepting three, which were used as background signal baseline controls. Substrate hydrolysis was monitored every 5 minutes for a total of 30 minutes. Substrate hydrolysis in the absence of inhibitor was linear for up to 15 minutes.

Inhibition of calpain I activity was calculated as the percent decrease in the rate of substrate hydrolysis in the presence of inhibitor relative to the rate in its absence. Comparison between the inhibited and control rates was made within the linear range for substrate hydrolysis. The IC₅₀s of inhibitors (concentration yielding 50% inhibition) were determined from the percent decrease in rates of substrate hydrolysis in the presence of five to seven different concentrations of the test compound. The results were plotted as percent inhibition versus log inhibitor concentration, and the IC₅₀ was calculated by fitting the data to the four-parameter logistic equation shown below using the program GraphPad Prism (GraphPad Software, Inc., San Diego, Calif.).

$$y = d + [(a-d)/(1+(x/c)^b)]$$

The parameters a, b, c, and d are defined as follows: a is % inhibition in the absence of inbibitor, b is the slope, c is the IC₅₀, and d is the % innibition at an infinite concentration of inhibitor.

Results are presented Table I below, which lists examples of the invention.

TABLE I

Calpain Inhibitory Activity.

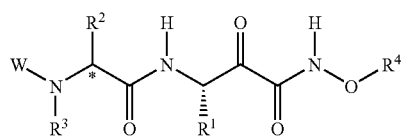

| Ex. | W | $R^1$ | $R^2$ | $R^3$ | $R^4$ | Calpain I $IC_{50}$ (nM) |
|---|---|---|---|---|---|---|
| 1 | BnOCO | Bn | L-$CH_2CH(CH_3)_2$ | H | $CH_3$ | 10 |
| 2 | BnOCO | Bn | L-$CH_2CH(CH_3)_2$ | H | $CH_2CH_3$ | 19 |
| 3 | BnOCO | Bn | L-$CH_2CH(CH_3)_2$ | H | Bn | 6 |
| 4 | BnOCO | Bn | L-$CH_2CH(CH_3)_2$ | H | $CH_2C_6F_5$ | 17 |
| 5 | BnOCO | Bn | L-$CH_2CH(CH_3)_2$ | H | tBu | 26 |
| 6 | BnOCO | Bn | L-$CH_2CH(CH_3)_2$ | H | (4-methyl-cyclohexyl) | 21 |
| 7 | $CH_3SO_2$ | $CH_2OCH_3$ | D-$CH_2OBn$ | H | Bn | 152 |
| 8 | $CH_3SO_2$ | Bn | D-$CH_2OBn$ | H | Bn | 28 |
| 9 | $CH_3SO_2$ | Bn | D-$CH_2OBn$ | H | $CH_2CH_3$ | 56 |
| 10 | BnOCO | Bn | L-$CH(CH_3)_2$ | H | Bn | 12 |
| 11 | BnOCO | $(CH_2)_3CH_3$ | L-$CH(CH_3)_2$ | H | Bn | 21 |
| 12 | Cbz-Leu | Bn | L-$CH_2CH(CH_3)_2$ | H | $CH_3$ | 20 |
| 13 | Cbz-Leu | Bn | L-$CH_2CH(CH_3)_2$ | H | Bn | 17 |
| 14 | PhCO | $(CH_2)_3CH_3$ | L-Bn | H | $CH_2CH_3$ | 193 |
| 15 | BnOCO | Bn | L-$CH_2CH(CH_3)_2$ | H | $(CH_2)_3CH_3$ | 183 |

It is intended that each of the patents, applications, and printed publications mentioned in this patent document be hereby incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:

1. A method for the treatment of stroke comprising administering to a subject in need of such treatment an effective amount of a compound of the Formula I:

wherein:
W is A-B-D;
A is aryl$(CH_2)_n$, heteroaryl$(CH_2)_n$, alkyl having from one to 14 carbons, alkenyl having from two to 14 carbons, or cycloalkyl having from 3 to 10 carbons, said A group being optionally substituted with one or more J groups;
B is a bond or CO, SO, $SO_2$, OCO, $NR^5CO$, $NR^5SO_2$, or $NR^5SO$;
D is a bond, an amino acid residue, or a peptide composed of 2 to 5 amino acid residues, said amino acid residue(s) being independently defined by the formula —NH-CH($R^6$)—CO—, in which  denotes the α carbon of an α-amino acid residue possessing, when $R^6$ is other than hydrogen, the D-configuration, the L-configuration, or a mixture of D- and L-;
n is an integer from 0 to 6;
$R^1$, $R^2$, $R^3$, $R^4$, $R^5$ and $R^6$ are, independently, hydrogen, alkyl having from one to about 14 carbons, or cycloalkyl having from 3 to about 10 carbons, said alkyl, and cycloalkyl groups being optionally substituted with one or more J groups; and
J is halogen, lower alkyl, aryl, heteroaryl, haloaryl, amino optionally substituted with one to three aryl or lower alkyl groups, guanidino, alkoxycarbonyl, amido, lower alkylamido, sulfonamido, lower alkyl sulfonamido, lower alkylsulfonyl, lower alkylsulfoxy, lower alkylthio, lower alkoxy, aryloxy, arylalkyloxy, hydroxy, carboxy, cyano, or nitro; and
* denotes the α carbon of an α-amino acid residue possessing, when $R^2$ is other than hydrogen, the D-configuration, the L-configuration, or a mixture of the D- and L-configurations.

2. The method of claim 1 wherein $R^1$ is alkyl or alkyl substituted with J, wherein J is lower alkoxy.

3. The method of claim 2 wherein $R^1$ is benzyl, methoxymethyl, or butyl.

4. The method of claim 1 wherein $R^2$ is alkyl or alkyl substituted with J, wherein J is arylalkyloxy or aryl.

5. The method of claim 2 wherein $R^2$ is isobutyl or benzyloxymethyl.

6. The method of claim 1 wherein $R^3$ is H.

7. The method of claim 1 wherein $R^4$ is alkyl, alkyl substituted with J, cycloalkyl, or cycloalkyl substituted with J wherein J is aryl, haloaryl, alkyl or heteroaryl.

8. The method of claim 7 wherein $R^4$ is methyl, ethyl, propyl, butyl, benzyl, (pentafluorophenyl)methyl, tert-butyl, or 4-methylcyclohexyl.

9. The method of claim 1 wherein W is benzyloxycarbonyl, methanesulfonyl, benzoyl, tert-butoxycarbonyl, or benzyloxycarbonyl-leucyl.

10. The method of claim 1 wherein $R^3$ is H, and $R^1$ is alkyl or alkyl substituted with J, wherein J is lower alkoxy.

11. The method of claim 1 wherein $R^3$ is H, and $R^2$ is alkyl or alkyl substituted with J wherein J is arylalkyloxy or aryl.

12. The method of claim 1 wherein $R^3$ is H, and $R^4$ is alkyl, alkyl substituted with J, cycloalkyl, or cycloalkyl substituted with J wherein J is aryl, alkyl, haloaryl, or heteroaryl.

13. The method of claim 1 wherein $R^3$ is H, $R^1$ is alkyl or alkyl substituted with J wherein J is lower alkoxy, and $R^2$ is alkyl or alkyl substituted with J wherein J is arylalkyloxy or aryl.

14. The method of claim 1 wherein $R^3$ is H, $R^1$ is alkyl or alkyl substituted with J, wherein J is lower alkoxy, and $R^4$ is alkyl, alkyl substituted with J, cycloalkyl, or cycloalkyl substituted with J wherein J is aryl, haloaryl, alkyl or heteroaryl.

15. The method of claim 1 wherein $R^3$ is H, $R^1$ is alkyl or alkyl substituted with J wherein J is lower alkoxy, $R^4$ is alkyl, alkyl substituted with J, cycloalkyl, or cycloalkyl substituted with J wherein J is aryl, haloaryl, alkyl or heteroaryl, and $R^2$ is alkyl or alkyl substituted with J wherein J is arylalkyloxy or aryl.

16. The method of claim 1 wherein $R^1$ is benzyl, methoxymethyl, or butyl; $R^2$ is isobutyl or benzyloxymethyl; $R^3$ is hydrogen; $R^4$ is methyl, ethyl, propyl, butyl, benzyl, (pentafluorophenyl)methyl, tert-butyl, or 4-methylcyclohexyl; and W is benzyloxycarbonyl, methanesulfonyl, benzoyl, tert-butoxycarbonyl, or benzyloxycarbonyl-leucyl.

17. The method of claim 1 wherein $R^1$ is benzyl; $R^2$ is isobutyl; * denotes the α carbon of an α-amino acid residue possessing the L-configuration; $R^3$ is hydrogen; $R^4$ is methyl, ethyl, propyl, butyl, benzyl, (pentafluorophenyl)methyl, tert-butyl, or 4-methylcyclohexyl; and W is benzyloxycarbonyl or benzyloxycarbonyl-leucyl.

18. The method of claim 1 wherein $R^1$ is benzyl; $R^2$ is benzyloxymethyl; * denotes the α carbon of an α-amino acid residue possessing the D-configuration; $R^3$ is hydrogen; $R^4$ is methyl, ethyl, or benzyl; and W is methanesulfonyl.

19. The method of claim 1 wherein W, $R^1$, $R^2$, $R^3$ and $R^4$ are selected in accordance with the following table:

| W | $R^1$ | $R^2$ | $R^3$ | $R^4$ |
|---|---|---|---|---|
| BnOCO | Bn | L—$CH_2CH(CH_3)_2$ | H | $CH_3$ |
| BnOCO | Bn | L—$CH_2CH(CH_3)_2$ | H | $CH_2CH_3$ |
| BnOCO | Bn | L—$CH_2CH(CH_3)_2$ | H | Bn |
| BnOCO | Bn | L—$CH_2CH(CH_3)_2$ | H | $CH_2C_6F_5$ |
| BnOCO | Bn | L—$CH_2CH(CH_3)_2$ | H | tBu |
| BnOCO | Bn | L—$CH_2CH(CH_3)_2$ | H | (4-methyl-cyclohexyl) |
| $CH_3SO_2$ | $CH_2OCH_3$ | D—$CH_2OBn$ | H | Bn |
| $CH_3SO_2$ | Bn | D—$CH_2OBn$ | H | Bn |
| $CH_3SO_2$ | Bn | D—$CH_2OBn$ | H | $CH_2CH_3$ |
| BnOCO | Bn | L—$CH(CH_3)_2$ | H | Bn |
| BnOCO | $(CH_2)_3CH_3$ | L—$CH(CH_3)_2$ | H | Bn |
| Cbz-Leu | Bn | L—$CH_2CH(CH_3)_2$ | H | $CH_3$ |
| Cbz-Leu | Bn | L—$CH_2CH(CH_3)_2$ | H | Bn |
| PhCO | $(CH_2)_3CH_3$ | L—Bn | H | $CH_2CH_3$ |
| BnOCO | Bn | L—$CH_2CH(CH_3)_2$ | H | $(CH_2)_3CH_3$. |

20. The method of claim 1 wherein
W is benzyloxycarbonyl;
$R^1$ is benzyl;
$R^3$ is H;
$R^2$ is L-$CH_2CH(CH_3)_2$ or L-$CH(CH_3)_2$;
and $R^4$ selected from the group consisting of —$CH_3$, —$CH_2CH_3$, benzyl, —$CH_2C_6F_5$, t-butyl, and 4-methylcyclohexyl.

* * * * *